US008461084B2

(12) United States Patent
Byrne et al.

(10) Patent No.: US 8,461,084 B2
(45) Date of Patent: Jun. 11, 2013

(54) HERBICIDAL MIXTURE, COMPRISING AN IMIDAZOLINONE HERBICIDE AND AN ADJUVANT

(75) Inventors: Thomas Byrne, Raleigh, NC (US);
Joseph Zawierucha, Cary, NC (US);
Charles W. Finch, Garner, NC (US);
Harold E. Quicke, Auburn, AL (US)

(73) Assignee: BASF Aktiengesellschaft, Ludwigshafen (DE)

( * ) Notice: Subject to any disclaimer, the term of this patent is extended or adjusted under 35 U.S.C. 154(b) by 1138 days.

(21) Appl. No.: 11/697,837

(22) Filed: Apr. 9, 2007

(65) Prior Publication Data

US 2007/0238618 A1    Oct. 11, 2007

Related U.S. Application Data

(60) Provisional application No. 60/789,892, filed on Apr. 7, 2006.

(51) Int. Cl.
*A01N 43/48*        (2006.01)

(52) U.S. Cl.
USPC ........................................ 504/253

(58) Field of Classification Search
None
See application file for complete search history.

(56) References Cited

U.S. PATENT DOCUMENTS

| 5,238,604 A | 8/1993 | Hazen et al. |
| 5,877,112 A * | 3/1999 | Roberts et al. ................ 504/206 |
| 5,973,154 A | 10/1999 | Drabb et al. |
| 6,339,158 B1 | 1/2002 | Wepplo et al. |

FOREIGN PATENT DOCUMENTS

| EP | 0 356 812 A2 | 3/1990 |
| EP | 356812 * | 3/1990 |
| JP | 52105213 | 9/1977 |
| JP | 2003040714 | 2/2003 |

OTHER PUBLICATIONS

International Search Report mailed Jul. 17, 2008.
Burnette, L. W., "Nonionics as Ionic Surfactant Intermediates," Nonionic Surfactants, Shick, M. ed., 1967, Chapter 11, pp. 372-394, Marcel Dekker, New York.
Farm Chemicals Handbook, 1997, Meister Publishing, p. C10.
The Pesticide Manual, 13th Ed. (2003), The British Crop Protection Council, pp. 1337-1344.
"Spray Adjuvant Overview," Weed Control Manual, 1998, vol. 31, Cover, table of contents and pp. 86-87.

* cited by examiner

*Primary Examiner* — Alton Pryor
(74) *Attorney, Agent, or Firm* — Rothwell, Figg, Ernst & Manbeck, P.C.

(57) ABSTRACT

A herbicidal mixture, comprising
a) a herbicidally effective amount of an imidazolinone herbicide selected from the group consisting of imazamox, imazapic, imazapyr;
b) an adjuvant comprising at least one of the following components: a partial phosphoric ester or a partial sulfuric ester of a monohydroxy-functional polyalkyl ether
and optionally
c) a further additive.

3 Claims, No Drawings

HERBICIDAL MIXTURE, COMPRISING AN IMIDAZOLINONE HERBICIDE AND AN ADJUVANT

DESCRIPTION

Cross Reference to Related Application

This application claims the benefit of U.S. Provisional 60/789,892, filed Apr. 7, 2006.

The present invention relates to a herbicidal mixture of an imidazolinone herbicide and an adjuvant.

The imidazolinone herbicides of the present invention encompass: imazamox, imazapic, imazapyr, all of those are further specified in e.g. C. D. S. Tomlin, "The Pesticide Manual", 13$^{th}$ Edition, BCPC (2003), Index 5, 1337-1344 and http://www.hcirss.demon.co.uk/index_cn_frame.html.

Refering to imidazolinone herbicides or specific imidazolinone herbicide species in this application shall mean the compounds as mentioned above, as well as their a) salts, e.g. salts of alkaline or earth alkaline metals or ammonium or organoammonium salts, for instance, sodium, potassium, ammonium, preferably isopropyl ammonium etc.; b) respective isomers, e.g. stereo isomers such as the respective enantiomers, in particular the respective R- or S-enantiomers (including salts, ester, amides), c) respective esters, e.g. carboxylic acid C1-C8-(branched or non-branched) alkyl esters, such as methyl esters, ethyl esters, isopropyl esters, d) respective amides, e.g. carboxylic acid amides or carboxylic acid C1-C8-(branched or non-branched) mono or di alkyl amides, such as dimethylamides, diethylamides, diisopropyl amides or e) any other derivative which contains the above imidazolinone structures as structural moiety.

In particular the term imidazolinone herbicide or reference to specific imidazolinone herbicides herein, such as, imazamox, imazapic, imazapyr, shall include alkylammonium salts, preferably isopropylammonium salts, for example diisopropylammonium- or monoisopropylammonium salts.

Further suitable imidazolinone herbicides are the R-isomers, e.g. R-imazamox, R-imazapic, R-imazapyr, in particular R-imazapyr. These compounds are known e.g. from U.S. Pat. No. 5,973,154 B (American Cyanamid Company) and U.S. Pat. No. 6,339,158 B1 (American Cyanamid Company).

EP 0 356 812 A2 discloses tank-mix compositions of certain herbicides, including imazaquin and imazethapyr, with low foaming nonionic alkylpolyoxyalkylene polyethers and for example anionic surfactants such as partial phosphate esters of monohydroxy-functional polyoxyalkylene ethers.

EP 0 356 812 A is silent as to weed control in the presence of trees.

It is an object of the present invention to provide a herbicidal mixture which comprises herbicidal mixtures of an imidazolinone herbicide and an adjuvant and whose herbicidal activity is higher than the activity of the pure active compound.

This object was achieved by a herbicidal mixture, comprising a) a herbicidally effective amount of an imidazolinone herbicide selected from the group consisting of imazamox, imazapic, imazapyr, b) an adjuvant comprising at least one of the following components: a partial phosphoric ester or a partial sulfuric ester of a monohydroxy-functional polyalkyl ether and optionally c) further additives.

The herbicidal mixture according to the invention displays a synergistic effect and is selective for those crop plants which are also compatible with the individual compounds.

Suitable adjuvants b) comprise partial phosphoric ester or partial sulfuric ester of a monohydroxy-functional polyalkyl ether.

These partial esters are prepared by methods well known to those skilled in the art, for example by reacting one of the well known and commercially monohydric polyoxyalkylene ethers with sulfuric acid or phosphoric acid or their chemical equivalents. The sulfate ester so obtained consist predominantly of the half ester (mono ester) while the phosphate esters generally contain both, mono- and diesters. Also usefull are the simple salts of these surfactants, for example, the alkali metal, alkaline earth metal or ammonium salts. The sulfate esters may be prepared for example by reacting a suitable mono-functional polyoxyalkylene ether with sulfuric acid or its chemical equivalent, preferably sulfamic acid or sulfurtrioxide. Phosphate esters are described, for example, in U.S. Pat. No. 5,877,112 column 2, lines 32 to 67 (included herein by reference) and may be prepared, for example, by reaction of the monofunctional polyoxyalkylene ether with phosphoric acid, diphosphorus pentoxide, polyphosphoric acid or phosphorus oxytrichloride. Methods of preparation are described in the treatise "Nonionic Surfactants", Martin Schick, Ed., Marcel Dekker, New York, 1967, chapter 11, pages 372-394.

Suitable partial phosphoric esters and partial sulfuric esters of a monohydroxy-functional polyalkylene ethers are those whose polyalkylene ether radicals can be prepared by oxalkylation of long-chain alcohols such as $C_{10}$-$C_{20}$-alkanols, preferably $C_{10}$-$C_{16}$alkanols, with alkylene oxides such as ethylene oxide, propylene oxide or butylene oxide. The alkylene oxides can be employed as a mixture, or else successively, for preparing block copolymers.

Preference is given to polyalkylene ethers having a $C_{10}$-$C_{16}$-alkyl chain with 10 to 15 mol of ethylene oxide units and 1 to 10, preferably 2 to 6 mol of propylene oxide units.

Preferred products are Klearfac™ AA 270 of BASF Corporation and Lutensit® A-EP from BASF Aktiengesellschaft.

The herbicidal mixture according to the invention comprises the components a) and b) in the following amounts (by weight-%): 1 to 99% by weight of the component a) and 1 to 99% by weight of the component b). Preferred ratios are: 20 to 80% by weight of the component a) and 20 to 80% by weight of the component b). Very preferred ratios are: 45 to 55% by weight of the component a) and 45 to 55% by weight of the component b). Here, the components together are 100% by weight.

In addition to component b), further additives c) can be used, alone or in combination, for example:

c1) castor oil based surfactant. This is a triglyceride ethoxylates—nonionic surfactant. Ethoxylated triglycerides are nonionic polyoxyethylene surfactants usually prepared by the condensation or addition of ethylene oxide to a hydrophobic compound, castor oil. Castor oil is a triglyceride (ester) of fatty acids with the approximate composition of 90% ricinoleic acid, an 18-carbon acid having a double bond in the 9-10 position and the hydroxyl group on the 12$^{th}$ carbon. The remaining 10% consists of linoleic, oleic, stearic, palmitic, dihydroxystearic, linolenic and eicosanoic acids;

c2) alkyl polyoxyalkylene polyethers. These compounds are known and many are commercially obtainable. These compounds are described, for example, in U.S. Pat. No. 5,238,604, col. 2, lines 43 to 68. Suitable alkyl polyoxyalkylene polyethers are those which can be prepared by oxalkylation of $C_{10}$-$C_{25}$-alkanols with alkylene oxides such as ethylene oxide, propylene oxide or butylene oxide. Preference is given to alkyl polyoxyalkylene polyethers having a $C_{10}$-$C_{25}$-alkyl chain, preferably $C_{12}$-$C_{20}$-alkyl chain, with an EO/PO block copolymer, such as, for example, Plurafac® LF, BASF AG, Plurafac RA 20® (BASF Aktiengesellschaft) and in particular Pluraflo L1060® (BASF Corporationn).

The present invention also extends to herbicidal compositions which comprise the components a) and b), optionally c), at least one liquid and/or solid carrier and, if desired, at least one further additive d).

Said herbicidal compositions can be a herbicidal finished formulation, preferably a herbicidal finished liquid formulation, most preferably a herbicidal finished aqueous liquid formulation.

However, these herbicidal compositions can also be tank-mixes which are made from the herbicidal mixture according to the invention or preferably from the herbicidal finished formulation according to the invention.

Such a tank mix is usually obtained by diluting the pre-mixed herbicidal mixture a) plus b) and optionally c) or preferably by diluting the finished formulation according to the invention, usually with water. Optionally further additives d) may be added before or after the mixing or dilution step.

Examples and brands of further additives d) are described in Farm Chemicals Handbook 1997; Meister Publishing 1997 p. C10 "adjuvant" or 1998 Weed Control Manual p. 86.

Preferably the tank-mix is prepared shortly before the application of the herbicidal composition.

A preferred further additive d) is methylated seed oil, such as methyl caprylate-caprate, methyl laurate, methyl myristate, methyl palmitate, methyl stearate, methyl oleate, methyl coconate, methyl sunflowerate, methyl canolate, and methyl soyate, in particular the one with the trade name Sunit II The methylated seed oils are known in the art and for example described in Fourth International Symposium on Adjuvants For Agrochemicals, Melbourne Australia, 1995, organized by The Counsel of Australian Weed Science Societies, Edited by Robyn E. Gaskin.

Methyl esters are usually produced by transesterification process: a natural fat (animal derived) or oil (vegetable derived) is combined with catalyst and methanol to yield, after refining, the whole methyl ester and a glycerine co-product. The whole methyl ester contains esters of all the fatty acids present in the fat or oil. It can be used as such or may be fractionally distlled into its components. Methylated seed oils are either saturated or unsaturated esters. The saturated esters range usually from C6 (caproate) to C18 (stearate), the unsaturated esters range usually from C14 (myristoleate) to C18 (linolenate).

Sunit II™ is a combination of methyl esters primarily methyl oleate with a proprietary nonionic surfactant.

The methylated seed oil can be added in amounts (all weight-%) from 0.5% to 50% preferably 1% to 20%, most preferably 1% to 10%, very most preferably 0.5% to 5%, all of those referring to % of adjuvant in water.

A herbicidal finished formulation according to the invention does include directly sprayable aqueous solutions, suspensions, highly-concentrated aqueous, oily or other suspensions or dispersions, emulsions, oil dispersions, pastes, materials for spreading, which can be applied by means of spraying, atomizing, spreading or pouring.

Suitable inert additives (auxiliaries), for example mineral oil fractions of medium to high boiling point such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, such as N-methylpyrrolidone and preferably water.

Aqueous use forms can be prepared from emulsion concentrates, suspensions, pastes, by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active substance, wetting agent, tackifier, dispersant or emulsifier and, if appropriate, solvent or oil, and these concentrates are suitable for dilution with water.

The concentrations of the herbicidal mixture a) and b) according to the invention in the herbicidal finished formulations can be varied within wide ranges. In general, the herbicidal finished formulations comprise from 0.01% to 95% by weight, preferably 0.5% to 90% by weight, very preferably 45% to 55% by weight of the herbicidal mixture a) and b) according to the invention.

A suitable herbicidal finished formulation according to the invention does in addition to the herbicidal mixture a) and b) comprise water.

Another suitable herbicidal finished formulation according to the invention does in addition to the herbicidal mixture a) and b) comprise water and an antifreeze agent. Anti-freeze agents are known in the art and include for example isopropylglycol, diisopropyl glycol, ethylene glycol.

Another suitable herbicidal finished formulation according to the invention does in addition to the herbicidal mixture a) and b) comprise water and an antifreeze agent, and the component a) being imazapyr, imazamox, imazapic or mixtures of those imidazolinone herbicides and the component b) being a partial phosphoric ester of a monohydroxy-functional polyalkyl ether, for example Klearfac® AA 270, a product of BASF Corporation, with or without alkyl polyoxyalkylene polyether.

A preferable herbicidal finished formulation according to the invention does in addition to the herbicidal mixture a) and b) comprise water and an antifreeze agent, and the component a) being imazapyr, imazamox or mixtures of those imidazolinone herbicides and the component b) being a partial phosphoric ester of a monohydroxy-functional polyalkyl ether, for example Klearfac® AA 270, a product of BASF Corporation, with or without alkyl polyoxyalkylene polyether.

Another preferable herbicidal finished formulation according to the invention does in addition to the herbicidal mixture a) and b) comprise water and an antifreeze agent, and the component a) being imazapyr and the component b) being a partial phosphoric ester of a monohydroxy-functional polyalkyl ether, for example Klearfac® AA 270, a product of BASF Corporation, with or without alkyl polyoxyalkylene polyether.

A very preferable herbicidal finished formulation according to the invention does in addition to the herbicidal mixture a) and b) comprise water and an antifreeze agent, and the component a) being imazapyr, imazamox, or mixtures of those imidazolinone herbicides and the component b) being a partial phosphoric ester of a monohydroxy-functional polyalkyl ether, for example Klearfac® AA 270, a product of BASF Corporation, wherein the components are contained in the following amounts, weight-% refering to the herbicidal finished formulation:
a) Imazapyr from 5% to 40%, preferably 10% to 20%; b) a partial phosphoric ester of a monohydroxy-functional polyalkyl ether, for example Klearfac® AA 270, a product of BASF Corporation from 5% to 50%, preferably 15% to 25%; and antifreeze agent: from 1% to 10%, preferably 1% to 5%; and water of the amount, which sums up to 100%.

The herbicidal finished formulation according to the invention does usually have a pH value in range from 6.0 to 8.0, in particular of from 6.8 to 7.2.

A big advantage of the herbicidal finished formulation according to the invention in which the imidazolinone herbicide is present in form of its salts, preferably of its ammonium salts and in particular of its monoisopropyl ammonium salt is that it does not need additional acid to buffer the formulation.

The herbicidal finished formulation according to the invention is generally prepared according to methods known in the art for the specific type of said formulations, see for example Surfactants & Specialities for Plant Protection Rhone-Poulenc (now Rhodia) $3^{rd}$ edition, 1994.

An example for a good method for the preparation of an aqueous herbicidal finished formulation according to the invention is as follows:

Usually about 90% of the total amount of water is added to the reactor vessel (about 10% is used at the end for active ingredient adjustment), then an amine, for example, monoisopropylamine is added to the reactor containing water, then the component a), for example imazapyr or imazamox is added to the reactor and blended until the reaction with the amine is complete, then the anti-freeze agent, for example, propylene glycol is added to the reactor and blended, then the additive b), for example Klearfac® AA 270 is slowly added to the reactor and blended until the pH is adjusted to 6.8 to 7.2. The batch is analyzed and the remaining water is added to achieve the active ingredient content of for example, 22.0%. All steps are usually conducted by a temperature of 20 to 25° C., if necessary by cooling the reaction vessel.

The components a) and b) are usually applied to the plants, their environment and/or seeds jointly. It is preferable to apply the active ingredients simultaneously. However, it is also possible to apply them separately.

The components a) and b) can be applied by using a herbicidal finished formulation or a tank-mix prepared as described above, preferably by using a herbicidal finished formulation.

Moreover, it may be advantageous to apply the herbicidal mixtures, herbicidal finished formulations or herbicidal compositions according to the invention with additional other crop protection agents, for example with pesticides or agents for controlling phytopathogenic fungi or bacteria. Also of interest is the miscibility with mineral salt solutions which are employed for treating nutritional and trace element deficiencies. Non-phytotoxic oils and oil concentrates can also be added, as described above.

The herbicidal mixtures, herbicidal finished formulations or herbicidal compositions according to the invention, can be employed, for example, in the form of directly sprayable aqueous solutions, suspensions, also highly-concentrated aqueous, oily or other suspensions or dispersions, emulsions, oil dispersions, pastes, materials for spreading or, by means of spraying, atomizing, spreading or pouring. Preferred is the application of directly sprayable aqueous solutions.

The use forms depend on the intended purposes; in any case, they should guarantee the finest possible distribution of the active ingredients according to the invention.

The herbicidal mixtures, herbicidal finished formulations or herbicidal compositions according to the invention can be applied pre- or post-emergence. It is advantageous to apply the herbicidal mixtures, herbicidal finished formulations or herbicidal compositions according to the invention post emergent when the crop has in general 1 to 6 leaves.

If the imidazolinone herbicide active ingredients are less well tolerated by certain crop plants, application techniques may be used in which the herbicidal compositions are sprayed, with the aid of the spray apparatus, in such a way that they come into as little contact, if any, with the leaves of the sensitive crop plants while reaching the leaves of undesirable plants which grow underneath, or the bare soil (post-directed, lay-by).

In the case of a post-emergence treatment of the plants, the herbicidal mixtures, herbicidal finished formulations or herbicidal compositions according to the invention are preferably applied by foliar application. Application may be effected, for example, by usual spraying techniques with water as the carrier, using amounts of spray mixture of approx. 47 to 473 l/ha. The mixtures or compositions may also be applied by the so-called "low-volume" and "ultra-low-volume" methods.

The rate of application of pure active ingredient a), i.e. without formulation auxiliaries, amounts in general to 0.1 to 2000 g/ha, preferably 1 to 1500 g/ha, in particular 5 to 1000 g/ha, of active substance (a.s.), depending on the intended aim, the season, the target plants and growth stage.

The herbicidal mixtures, herbicidal finished formulations or herbicidal compositions according to the invention can effect very good control of grass weeds and broadleaf weeds in many crops without damaging the crop plants, an effect observed especially at low rates of application.

Suitable crops are for example maize, *brassica napus* (canola, oilseed rape), sunflower, legumes, sugar cane, and soya, or cereals (for example wheat, rye).

The herbicidal mixtures, herbicidal finished formulations or herbicidal compositions according to the invention can advantageously been used to very good control undesired vegetation in non-crop areas such as roads, railroads, turf, utility lines, and in particular in areas in which trees are present. The herbicidal mixtures, herbicidal finished formulations or herbicidal compositions according to the invention are preferably used in forestry.

Undesired vegetation in non-crop areas which is controlled by the herbicidal mixtures, herbicidal finished formulations or herbicidal compositions according to the invention does include the following grasses of Table 1

TABLE 1

Annual bluegrass (*Poa annua*)
Bahiagrass (*Paspatum notatum*)
Barnyardgrass (*Echinocloa crus-gall*)
Beardgrass (*Andropogon* spp.)
Bermudagrass (*Cynodon dactylon*)
Big bluestern (*Andropogon gerardi*)
Broacleaf sinalgrass (*Brachiaria platyphylia*)
Canada bluegrass (*Poa compressa*)
Cattal (*Typha* spp.)
Cheat (*Bromus secalinus*)
Congograss (*Imperata cylindrica*)
Crabgrass (*Digitaria* spp.)
Crowfootgrass (*Dactyloclenium aegyptium*)
Dallisgrass (*Paspatum dilatatum*)
Downy brome (*Bromus tectorum*)
Fall panicum (*Panicum dichotomiflorum*)
Feathertop (*Pennisetum vilosum*)
Fescue (*Festuca* spp.)
Foxtail (*Setaria* spp.)
Giant reed (*Arundo donax*)
Goosegrass (*Enusine indica*)
Guineagrass (*Panicum maximum*)
Italian ryegrass (*Lolium multiflorum*)
Itchgrass (*Rottbolia exaltata*)

TABLE 1-continued

Johnsongrass (*Sorghum haltepense*)
Junglerice (*Echinochloa colorum*)
Kentucky bluegrass (*Poa pratensis*)
Lovgrass (*Eragrostis* spp.)
Orchardgrass (*Dactytis glomerata*)
*Panicum* spp.
Paragrass (*Brachiaria mutica*)
Phragmites (*Phragmites australis*)
Praline cordgrass (*Spartina pectinata*)
Prairie threeawn (*Aristida oligantha*)
Quackgrass (*Agropyron repans*)
Reed canary grass (*Phataris arundinacea*)
Saltgrass (*Distichis stricta*)
Sand dropseed (*Sporobolus cyptandrus*)
Sandbur (*Cenchrus* spp.)
Smooth brome (*Bromus inermis*)
Sprangletop (*Leptocloa* spp.)
Timothy (*Pheum pratense*)
Torpedograss (*Panicum repens*)
Vaseygrass (*Paspatum urvilli*)
Wild barley (*Hordeum* spp.)
Wild oats (*Avena fatua*)
Wirestern muhly (*Muhlenbergia frondosa*)
Witchgrass (*Panicum capillare*)
Woolly cupgrass (*Eriochloa wilosa*)

And the following broad leaf weeds of Table 2:

TABLE 2

Arrowwood (*Pluchea sericea*)
Broom snakeweed (*Guterrazia sarothrae*)
Bull Thistle (*Cirsium vulgare*)
Burclover (*medicago* spp.)
Burdock (*Arctium* spp.)
Camphorweed (*Heterotheca subaxilaris*)
Carolina geranium (*Geranium carolinarum*)
Carpetweed (*Mulogo verticitata*)
Chickweed, moussear (*Cerastium vulgatum*)
Clover (*Trifolium* spp.)
Cocklebur (*Xanthium strunarium*)
Common chickweed (*Stellaria media*)
Common ragweed (*Ambrosia artemisifolia*)
Cudweed (*Gnaphalium* app.)
Dandelion (*Taraxacum officinale*)
Desert camelthorn (*Alhegi pseudahagi*)
Diffuse knapweed (*Cantauree diccusal*)
Dock (*Rumex* spp.)
Dongfennel (*Eupatorium capillfolium*)
Giant ragewood (*Ambrosia trifida*)
Fiddleneck (*Amsinckia intermedia*)
Filaree (*Erodium* spp.)
Fleebane (*Erigeron* spp.)
Goldenrod (*Solidago* spp.)
Gray rabbitbrush (*Chrysothamus nauseosus*)
Henbit (*Lamium aplexicante*)
Hoary vervain (*Verbena stricta*)
Horseweed (*Conyza canedensia*)
Indian mustard (*Brassica junceea*)
Japanese bamboo/knotweed (*Polygonum cuspidatum*)
Knotweed prostrate (*Polygonum aviculare*)
Kochia (*Kochia sooparia*)
Lambsquarters (*Chenopodium album*)
Little mallow (*Malva parviflora*)
Mikeweed (*Ascelipas* spp.)
Miners lettuce (*Montia perfollata*)
Nottleleaf goosefoot (*Chenopodium murale*)
Oxeye daisy (*Chrysanthenum leucantherum*)
Pepperweed (*Iepidum* spp.)
Pigweed (*Amaranthus* spp.)
Plantain (*Plantego* spp.)
Pokeweed (*Phytolacca americana*)
Primrose (*Cenothera kunthiana*)
Puncturevine (*Tribuius terrestris*)
Purple loose strife (*Lynthrum salicaria*)
Purslane (*Portulaca* spp.)
Pusley, Florida (*Richardia scabra*)
Rocket, London (*Sisymbrium Irio*)

TABLE 2-continued

Rush skeletonweed (*Chondrilla juncea*)
Russian knapweed (*Centaurea repans*)
Russian thistle (*Saisol kali*)
Saltbush (*Atriplex* spp.)
Shephered's purse (*Capsella bursa-pastoris*)
Silverleaf nightshade (*Solanum elesagnifolum*)
Smartweed (*Polygonum* spp.)
Sorrel (*Rumex* spp.)
Sowthistle (*Sonchus* spp.)
Spurge annual (*Euphorbia* spp.)
Stinging nettle (*Urtica dioica*)
Sunflower (*Helianthus* spp.)
Tansymustard (*Descurainia pinnata*)
Sweet clover (*Melitotus* spp.)
Texas thistle (*Cirsium texanum*)
Velvetleaf (*Abutilon theophrasti*)
Western ragwood (*Ambrosia palliostachya*)
Wild carrot (*Daucus carota*)
Wild lettuce (*Lactuca* spp.)
Wild parship (*Pastinaca sativa*)
Wild turnip (*Brassica campestris*)
Woolyleaf bursale (*Ambrosia grail*)
Yellow starthistle (*Cantaurea solstialis*)
Yellow woodsorrel (*Oxalis stricta*)

The invention is further illustrated by the following examples.

EXAMPLES

Imazapyr Uptake and Translocation

The enhanced herbicidal effect is directly correlated to the uptake and the translocation of the herbicidal mixture according to the invention in plants In the following experiments the uptake was tested. v/v means volume by volume. ARSENAL® and CHOPPER® are Tradenames of BASF Corporation. MSO means methylated seed oil.

Example I

Methodology

Arsenal AC Soluble Liquid (SL) herbicide was combined with different surfactants at two rates (0.25% and 2% v/v) and compared to Arsenal AC and Chopper Soluble Liquid (SL) herbicide without surfactant or with 12.5% MSO.

Arsenal AC is a surfactant free formulation of imazapyr containing 0.48 kg ai/1 l. Chopper contains an emulsifier and 0.24 kg ai imazapyr per liter.

MSO is approximately 0.85 kg/l seed oil and 0.15 kg/l nonionic surfactant.

Rates used were 0.71 l Arsenal AC and 1.42 l Chopper, equivalent to 0.84 kg imazapyr per hectare.

The surfactants are: PLURAFLO® L-1060 or KLEARFAC® AA-270

Treatments were applied to water oak (*Quercus nigra*). Water oak is a relatively hard to control species.

Plants were presprayed with cold formulations at 0.84 gram per hectare within a few hours of radiotracer application. Once the pre-spray dried, two of the uppermost fully expanded leaves received 2.4 µl of radiolabeled formulation. One hour after application (HAT), one treated leaf was removed and washed with 3-5 ml distilled water rinses, with a 5 ml funnel rinse collected in the same vial. The washed treated leaf was then bagged and frozen for later oxidation. One week after treatment (WAT) the final harvest began with removal and water washing of the remaining treated leaf (same as HAT leaf). The plant was clipped at the root collar and the above ground portion oven dried (stem). The roots were washed of potting soil and oven dried. Once dried, the above- and below-ground plant portions were ground in a coffee mill and subsampled. The water wash was analyzed using a 1 ml aliquot combined with Scintiverse II liquid scintillation cocktail, counted on a Packard Tri Carb 2900 TR Liquid Scintillation Counter (LSC). The treated leaves were oxidized in an OX-500 Harvey Biological Oxidizer, which converts carbon-14 to $CO_2$ in liquid to be counted on the LSC. The stem and root subsamples were also oxidized on the OX-500 and counted.

Imazapyr Uptake and Translocation Results

Experiment 1.1: KLEARFAC® AA-270 Response vs. Water Oak (*Quercus Nigra*)

| Species | Rate | Adjuvants | Washoff | Root + Stem | Leaf |
|---|---|---|---|---|---|
| Water oak | 0.00% | No adjuvants | 62 | 2.2 | 27.1 |
|  | 0.25% | Klearfac AA 270 | 54 | 2.3 | 37.0 |
|  | 2.00% | Klearfac AA 270 | 31 | 3.3 | 53.0 |

Imazapyr Uptake. Numbers in the table above are the percent of applied imazapyr. Washoff numbers are for the one week after treatment assessment.

Conclusion

Phosphate esters reduce the washoff while increasing the root+stem and leaf concentration of imazapyr. Improved Root+Stem and Leaf uptake are noted with increased rate of KLEARFAC® AA-270.

Experiment 1.2: Pluronic Block Polymers+Phosphate Esters vs. Imazapyr Uptake.

| Species | PLURAFLO 1060: KLEARFAC AA270 Ratio | Washoff* 0.25% | Washoff* 2.0% | Root + Stem 0.25% | Root + Stem 2.0% | Leaf 0.25% | Leaf 2.0% |
|---|---|---|---|---|---|---|---|
|  |  |  | % of applied |  |  |  |  |
| Water oak | 100:0 | 54 | 61 | 2.0 | 3.3 | 33.5 | 27.0 |
|  | 90:10 | 59 | 57 | 2.1 | 4.0 | 29.7 | 33.6 |
|  | 70:30 | 59 | 59 | 2.3 | 3.0 | 31.5 | 30.6 |
|  | 50:50 | 48 | 45 | 2.1 | 2.9 | 39.5 | 42.1 |
|  | 0:100 | 54 | 32 | 2.3 | 3.4 | 36.9 | 52.1 |
|  | No adjuvant | 62 | 62 | 2.2 | 2.2 | 27.1 | 27.1 |

*Washoff, Root + Stem and Leaf numbers are for the one week after treatment assessment.

Conclusions:

Phosphate esters and blends with Pluronic type surfactants reduce the washout while increasing the root+stem and leaf concentration of imazapyr.

A blend of Pluraflo 1060 and Klearfac AA 270 provides increased uptake. For example, in the wash off, root+stem, and leaf improve with increased concentration of the adjuvant.

Example II

Imazapyr Absorption

Methodology

Arsenal® AC herbicide was combined with different surfactants at one rate (50% v/v), alone and with 1.0% v/v MSO. This was compared to Chopper® herbicide without surfactant alone and with 1.0% v/v MSO.

Arsenal AC is a surfactant free formulation of imazapyr containing 0.48 kg/l.

Chopper contains an emulsifier and 0.24 kg/l imazapyr per gallon.

MSO is approximately 0.85 kg/l seed oil and 0.15 kg/l nonionic surfactant.

The absorption was measured by the relative percent of injury compared to Chopper alone and with MSO. Rates used were 320 g active ingredient/ha. Treatments were applied to imi-tolerant sunflowers, a relatively hard to control species. The surfactants are listed below:

| ID Code | Surfactant | Chemical Description | Provider |
|---|---|---|---|
| A-4 | Berol DGR 81 | Caster oil based blended surf. | Akzo Nobel |
| B-4 | Klearfac AA 270 | Alcohol alkoxylate phoshate ester | BASF Corporation |
| B-6 | Plurafac RA 20 | Linear alcohol ethoxylate | BASF AG |

Imazapyr Absorption Results

Formulation without MSO

| | % Increase Absorption | |
|---|---|---|
| Form ID | 7 DAT | 20 DAT |
| Check | 0 | 0 |
| Chopper | 0 | 0 |
| A-4 | 30.0 | 10.0 |
| B-4 | 69.7 | 76.3 |
| B-6 | 33.3 | 40.0 |

Formulation Plus MSO

| | % Increase Absorption | |
|---|---|---|
| Form ID | 7 DAT | 20 DAT |
| Chopper | 60.0 | 40.0 |
| B-4 | 80.0 | 73.3 |

We claim:

1. A herbicidal finished formulation consisting essentially of
    a) a herbicidally effective amount of imazapyr, wherein the imazapyr is present in an amount from 5% to 40%; and
    b) a partial phosphoric ester of a monohydroxy-functional polyalkyl ether wherein the partial phosphoric ester of monohydroxy-functional polyalkyl ether is present in an amount from 5% to 50%;
    c) an antifreeze agent; and
    d) water.

2. The herbicidal finished formulation according to claim 1, wherein said imazapyr is in an amount from 5% to 40%, said partial phosphoric ester of a monohydroxy-functional polyalkyl ether is in an amount from 5% to 50%, and said antifreeze agent is in an amount from 1% to 10%.

3. The herbicidal finished formulation according to claim 2, wherein said imazapyr is in an amount from 10% to 20%, said partial phosphoric ester of a monohydroxy-functional polyalkyl ether is in an amount from 15% to 25%, and said antifreeze agent is in an amount from 1% to 5%.

* * * * *